United States Patent

Morii et al.

[11] Patent Number: 5,110,736
[45] Date of Patent: May 5, 1992

[54] PURIFICAITON PROCEDURE OF TPA FROM CRUDE PREPARATIONS

[75] Inventors: Mitsuyoshi Morii; Masaharu Ohoka, both of Yokohama; Nobuhiro Kawashima, Sagamihara; Noriko Morii, Yokohama; Toshihiko Suzuki, Tokyo, all of Japan

[73] Assignee: Mitsui Toatsu Chemicals, Incorporated, Tokyo, Japan

[21] Appl. No.: 602,387

[22] Filed: Oct. 24, 1990

Related U.S. Application Data

[63] Continuation of Ser. No. 287,655, Dec. 21, 1988, abandoned, which is a continuation of Ser. No. 887,514, Jul. 21, 1986, abandoned.

[30] Foreign Application Priority Data

Aug. 1, 1985 [JP] Japan ............... 60-168601

[51] Int. Cl.$^5$ ............................................. C12N 9/64
[52] U.S. Cl. .................................. 435/226; 435/212; 435/219
[58] Field of Search ............... 435/226, 212, 215, 217, 435/219

[56] References Cited

FOREIGN PATENT DOCUMENTS 0112122  6/1984  European Pat. Off. ............ 435/226
0143081  5/1985  European Pat. Off. .

OTHER PUBLICATIONS

Chemical Abstracts, vol. 102, No. 1, Jan. 7, 1985, p. 238 Abstract No. 2474f, C. Heussen et al "Purification of Human Tissue . . . ".

Kluft, C. et al., (1983) Advances in Biotechnological Processes, vol. 2, pp. 97-110, A. R. Liss, Inc, N.Y. (Mizrahi and van Wezel, editors).

*Primary Examiner*—Charles L. Patterson
*Attorney, Agent, or Firm*—Nixon & Vanderhye

[57] ABSTRACT

Crude tPA containing, as an impurity, a protein which is reactive with an anti-human tPA antibody and has a molecular weight of 110,000±20,000 daltons is purified by bringing the crude tPA into close contact with an affinity reagent containing an immobilized Kunitz inhibitor which is produced in seeds of *Erythrina latissima* and other Erythrina plants and acts as an inhibitor on trypsin, plasmin and tPA but does not act on urokinase, so that tPA is collected selectively.

10 Claims, No Drawings

PURIFICAITON PROCEDURE OF TPA FROM CRUDE PREPARATIONS

This is a continuation of application Ser. No. 07/287,655, filed Dec. 21, 1988, now abandoned. This is a continuation of application Ser. No. 06/887,514, filed Jul. 21, 1986, now abandoned.

BACKGROUND OF THE INVENTION

1. Field of the Invention

This invention relates to a method for the purification of tissue plasminogen activator (tPA), and more specifically to a method for obtaining tPA in an isolated and purified form by treating crude tPA with a specific tPA inhibitor.

2. Description of the Prior Art

Tissue plasminogen activator (tPA) means a sort of protein which is produced in a tissue of a higher animal and serves to activate plasminogen, a precursor for plasmin which is a proteolytic enzyme specific to fibrin.

tPA is similar to urokinase in many aspects but also different from urokinase in many aspects. Since tPA has significant potential utility as a thrombolytic drug, intensive researches are now under way at various places as to its preparation process.

tPA was previously obtained by separating it from cultured renal cell broth. This method is however inappropriate for obtaining tPA in a large amount. The culture of specific cell, which secrete tPA in a still greater amount, and the isolation of the resulting tPA are the subjects of a great deal of work these days.

SUMMARY OF THE INVENTION

This invention has been brought to completion in the course of a research conducted by the present inventors in the light of the above-mentioned trend. It is an object of this invention to provide a method which can furnish purified tPA in a large amount.

In one aspect of this invention, there is provided a method for the purification of crude tPA containing, as an impurity, a protein which is reactive with an anti-human tPA antibody and has a molecular weight of 110,000 ± 20,000 daltons, which comprises bringing the crude tPA into close contact with an affinity reagent containing an immobilized Kunitz inhibitor which is produced in seeds of *Erythrina latissima* and other *Erythrina* plants and acts as an inhibitor to trypsin, plasmin and tPA but not to urokinase, so that tPA is collected selectively.

The above-mentioned object of this invention has been attained by the method of this invention.

The above and other objects, features and advantages of the present invention will become clear from the following detailed description and the appended claims.

DETAILED DESCRIPTION OF THE INVENTION AND PREFERRED EMBODIMENTS

This invention includes as its principal feature the removal of a certain particular impurity, the admixture of which is attributed to the use of a culture medium added with fetal calf serum, by using a specific tPA inhibitor.

As specifically described above, the method of this invention makes use of "an immobilized Kunitz inhibitor which is produced in seeds of *Erythrina latissima* and other *Erythrina* plants and acts as an inhibitor to trypsin, plasmin and tPA but not to urokinase".

Use of the above inhibitor for the purification of tPA has itself been already known in European Patent Publication No. 112122-A.

In the above prior art, human melanoma cells are allowed to grow as a monolayer deposited on the RPMI (Rosswell Park Memorial Institute) 1640 tissue culture medium which contains 10% of thermoinactivated (56° C., 30 minutes) fetal calf serum (FCS). The cultured cell is washed once and then covered with a serum-free medium. Twenty four hours later, the medium is harvested and then treated with an affinity reagent containing an immobilized Kunitz inhibitor which is produced in seeds of *Erythrina latissima* and other *Erythrina* plants and acts as an inhibitor to trypsin, plasmin and tPA but not to urokinase.

In the prior art process, FCS is used in the cell growth stage of tPA-producing but the tPA-secreting stage is carried out after washing the cells once and removing FCS. The prior art process is therefore free from the problem of the specific impurities in the solution of which problem is the principal target of the present invention.

Although the present invention is similar in constitution to the above-described prior art, the present invention has solved the new technical problem which was not involved in the prior art. The present invention cannot therefore be created easily on the basis of the prior art.

The present inventors investigated the behavior of tPA contained in a cultured melanoma cell broth, which had been obtained by using the RPMI 1640 culture medium with 10% of FCS contained therein, by zymography after SDS polyacrylamide gel electrophoresis, and compared it with that of tPA obtained without addition of fetal calf serum.

According to this comparison, a band of a protein which is reactive with an anti-human tPA antibody and has a molecular weight of 110,000 ± 20,000 daltons is observed besides tPA having a molecular weight of 70,000 daltons in the case of the serum-added culture medium. This band may also be observed barely even in the case of the serum-free culture medium but the amount of the protein is much greater in the serum-added culture medium.

This tendency is observed not only in the culture of melanoma cells but also in the culture of cells derived from a normal human tissue or cells obtained by integrating the human tPA gene using the recombinant DNA technology. Namely, the protein is considered to be a conjugated protein of tPA and a binding protein to tPA derived from FCS contained in the culture medium. Since the protein is a conjugated protein of a protein of a different species and tPA, the conjugated protein becomes an immunogen to patients if it is mixed in a purified tPA specimen. Even if this tPA-conjugated protein is contained in an aqueous solution, it is not adsorbed on any immobilized inhibitor. In the method of this invention, it is hence possible to use an affinity reagent to remove the tPA-conjugated protein together with unadsorbed impurities when tPA is contaminated by the tPA-conjugated protein.

In a preferred embodiment, animal cells with the human tPA gene incorporated therein by the recombinant DNA technology are cultured, so that the problem of admixture of one or more tPA contaminants derived from the host cells can be overcome although their admixture is worried whenever tPA is produced by using cells of an animal other than human.

When cells other than human cells are chosen as host cells and the thus-chosen cells produce tPA particular to the cells, this particular tPA is believed to induce an immunoreaction to patients.

The affinity reagent containing the specific inhibitor, which is useful in the practice of the present invention, can surprisingly separate human cell derived tPA and host cell derived tPA from each other for the collection of the former tPA in accordance with the method invented by the present inventors.

This is also a subject or feature not dealt with in the above-described prior art, because it was only tPA secreted from melanoma cells that was dealt with in the prior art.

When passing an aqueous medium, which contains both recombinant tPA and host cell derived tPA, through a layer of an affinity reagent, a 0.5-3.0M (for example, 1.0-2.0M, preferably 1.5M) saline is used. Here, the saline may preferably have a pH near the neutral level and may desirably contain a suitable stabilizing amount of a surface active agent [for example, "Tween" (trade mark) or "Triton X-100" (trade name) in an amount of 0.1%]. Under these conditions, the recombinant tPA is adsorbed on the layer of the affinity reagent but the host cell derived tPA is not adsorbed thereon.

For the desorption of tPA, the conventionally-known method (see, European Patent Publication No. 112122-A) can be employed.

As has been described above, the present invention is directed to the application of the affinity reagent containing an immobilized Kunitz inhibitor, which is produced in seeds of *Erythrina latissima* and other *Erythrina* plants and acts as an inhibitor to trypsin, plasmin and tPA but not to urokinase, for the purification of tPA. Owing to this new technique of the present invention, it has now become possible to separate and remove two impurities, i.e., a substance which is reactive with an anti-human tPA antibody and has a molecular weight of 110,000 ± 20,000 daltons, and host cell derived tPA which raises a problem whenever tPA is produced by using the recombinant DNA technology.

The substance which is reactive with an anti-human tPA antibody and has a molecular weight of 110,000 ± 20,000 daltons cannot of course be removed by an affinity reagent containing an immobilized anti-human tPA antibody. Even if the gel filtration method is relied upon, it cannot be completely separated because the reactivity of tPA to a resin affects adversely on the resolution capacity of the resin.

Since host cell derived tPA has the same molecular weight as human tPA, it seems to be no choice other than using an affinity reagent with a monoclonal antibody capable of identifying the host cell derived tPA unless the method of this invention is used. Preparation of this monoclonal antibody however requires both time and labor and the above-mentioned method has low practical utility.

The present invention has great significance in that the above-mentioned serious problems, which arise upon utilization of tPA, have been solved at a stroke by its simple method.

The affinity reagent employed in the present invention for the purification of tPA reacts not only with tPA but also with trypsin and plasmin and inhibits them owing to its specificity. However, this property becomes a problem for the purification of tPA when a cultured broth of tPA-producing cells is contaminated with trypsin and plasmin. When an inhibitor of such a type that inhibits trypsin and plasmin but not tPA, for example, a trypsin inhibitor derived from soybeans, i.e., α-2-plasmin inhibitor or aprotinin is added to the cultured broth in advance, trypsin and plasmin are coupled with these inhibitors to form conjugated proteins and become no longer reactive with the affinity reagent employed in the present invention, thereby facilitating their removal.

As has been described above, the affinity reagent of this invention containing an immobilized Kunitz inhibitor, which is produced in seeds of *Erythrina latissima* and other *Erythrina* plants and acts as an inhibitor to trypsin, plasmin and tPA but not to urokinase, has been found to be superior in reaction specificity, binding capacity to tPA, stability upon application and utility to the tPA purification method when the affinity reagent is used in accordance with the improved method of this invention.

EXAMPLE 1:

Preparation of an affinity reagent

The affinity reagent employed as an inhibitor in the present invention was prepared in the following manner.

In accordance with the method proposed by Joubert et al., seeds of *Erythrina latissima* were collected and prepared. Ground and defatted seeds were extracted overnight at 10° C. with a 0.5M aqueous solution of NaCl. The extract was centrifuged and the intended substance was collected from the supernatant by precipitating with ammonium sulfate. The thus collected substance was subjected to chromatography on "Sephadex G50 (trade name)", DEAE-cellulose and "DEAE-Sepharose (trade mark)". The final purified product migrated as a single band of apparent molecular weight of 22,000 daltons when subjected to electrophoresis in a 15% polyacrylamide gel containing 0.1% of sodium dodecylsulfate (SDS).

The purified product (26 mg) was bound on 5 ml of commercial BrCN-activated agarose. The affinity reagent was equilibrated with a phosphate buffer which contained 0.4M of NaCl, 0.1% of "Triton X-100" (trade name; a commercial surface active agent employed routinely in the present field of art) and 0.02% of sodium azide as a stabilizer and had a pH of 7.4. This affinity reagent was packed in 5-ml columns which had been formed of disposal plastic syringes.

Purification of tPA from crude tPA containing an impurity having a molecular weight of 110,000 daltons After stabilizing with 0.02% of "Tween 80" (trade name) 2 l of a spent medium which had been obtained from Bowes melanoma cells (ATCC CRL 1424 G 361) with culture medium containing 10% of thermoinactivated (56° C., 30 minutes) fetal calf serum and 20 KI-U/m( of aprotinin, it was subjected to one of the above-prepared affinity columns.

The column effluent was collected and the plasminogen-dependent fibrinolytic activity was measured.

About 10% of the activity applied to the column was observed.

This fraction was analyzed by zymography after SDS polyacrylamide gel electrophoresis. As plasminogen activators, two kinds of substances were confirmed, one having a molecular weight of 110,000 ± 20,000 daltons and the other being in an small amount and having a molecular weight of 70,000 daltons.

After passing the whole spent medium through the to the column capacity) of a 0.1M $NH_4HCO_3$ buffer (pH 7.5) which contained 1.0M NaCl and 0.2% of "Tween 80". By this method, about 3% of the activity applied to the column was detected. A band corresponding to 110,000 ± 20,000 daltons and another band corresponding to 70,000 daltons, which was weaker than the former band, were confirmed as plasminogen activators on a zymograph.

The thus-adsorbed protein was eluted with a 0.1M glycine hydrochloride buffer (pH 3.5) containing 0.1M NaCl. In this manner, the remaining plasminogen-dependent fibrinolytic activator was eluted. It was observed as a sharp peak. This peak was in conformity with the peak of the protein.

This fraction showed 80–85% of the activity applied to the column. It was a single band of a protein having a molecular weight of 70,000 daltons.

EXAMPLE 2

After stabilizing with 0.02% of "Tween 80" (trade name) 2 l of a cultured broth of human fetal foreskin cells (Flow 7000) which contained 10% of thermoinactivated (56° C., 30 minutes) fetal calf serum and 20 KI-U/m( of aprotinin, it was subjected to one of the above-prepared affinity columns.

The column effluent was collected and the plasminogen-dependent fibrinolytic activity was measured. About 45% of the activity applied to the column was observed.

This fraction was analyzed by zymography after SDS polyacrylamide gel electrophoresis. As plasminogen daltons, 2–3 bands around 50,000–70,000 daltons, and one band near 35,000 daltons.

After passing the whole cultured medium through the column, the column was washed with 20 volumes (relative to the column capacity) of a 0.1M $NH_4HCO_3$ buffer (pH 7.5) which contained 1.0M NaCl and 0.2% of "Tween 80". By this method, about 5% of the activity applied to the column was detected. The same bands as those observed above were found on a zymograph.

The thus-adsorbed protein was eluted with a 0.1M glycine hydrochloride buffer (pH 3.5) containing 0.1M NaCl. In this manner, the remaining plasminogen-dependent fibrinolytic activator was eluted. It was observed as a sharp peak. This peak was in conformity with the peak of the protein. This fraction showed 40–50% of the activity applied to the column. It was a single band of a protein having a molecular weight of 70,000 daltons.

EXAMPLE 3

The adsorption and elution behavior of tPA, which had been produced by using Chinese hamster ovary (CHO) cells as host cells for recombination, was investigated.

After stabilizing with 0.02% of "Tween 80" (trade name) 2 % of a cultured broth of non-recombinant CHO cells (CHO-K, ATCC CCL 61) which contained 10% of thermoinactivated (56° C., 30 minutes) fetal calf serum, it was subjected to one of the affinity columns prepared in Example . The tPA activity contained in the cultured broth was about 0.2 U/ml.

The column effluent was collected and the plasminogen-dependent fibrinolytic activity was measured. No tPA was however detected.

After passing the whole cultured broth through the column, the column was washed with 20 volumes (relative to the column capacity) of a 0.1M $NH_4HCO_3$ buffer (pH 7.5) which contained 1.5M NaCl and 0.2% of "Tween 80". By this method, the plasminogen-dependent fibrinolytic activity was measured. No tPA was detected.

The column was thereafter washed with 10 volumes (relative to the column capacity) of a 0.1M glycine hydrochloride buffer (pH 3.5) containing 0.1 M NaCl, which was an eluent for human tPA.

No tPA was detected in this fraction.

Thereafter, desorption of tPA was attempted with 10 volumes (relative to the column capacity) of a 0.1M Tris-HCl buffer (pH 9.0) which contained 3M of ammonium thiocyanate and 0.2% of "Tween 80". Almost 100% of the activity applied to the column was detected by this method. Subsequent to its electrophoresis in an SDS-containing polyacrylamide gel, tPA having a molecular weight of 70,000 daltons was detected by zymography.

As demonstrated above, CHO cell derived tPA and human tPA exhibited different adsorption and desorption behavior to the affinity reagent.

For convincing this fact, chinese hamster tPA obtained by the method described above was labeled with $I^{125}$, followed by its addition to 0.5 l of cultured medium of CHO cels in which the human tPA cDNA gene had been integrated by the following method. Expression of tPA had been achieved in CHO cells by cotransfection and subsequent coamplification of the transfected sequences. Expression vectors containing human tPA cDNA gene and a dihydrofolate reductase (DHFR) cDNA gene were cotransfected into CHO DHFR-deficient cels. Transformants expressing DHFR were selected by growth in media lacking nucleosides and contained low numbers of tPA genes and DHFR genes. Stepwise selection of the DHFR+transformants in increasing concentrations of methotrexate generated cels which had amplified both DHFR genes and tPA genes over 100-fold. These cell lines expressed elevated levels of enzymatically active tPA.

The cultured medium contained 10% of thermoinactivated (56° C., 30 minutes) fetal calf serum was stabilized with 0.02% of "Tween 80". The solution was applied to one of the above-prepared column. After washing the column with a 0.1M $NH_4HCO_3$ buffer (pH 7.5) which contained 5M of NaC and 0.2% of "Tween 80", the protein was eluted with a 0.1M glycine hydrochloride buffer (pH 3.5) containing 0.1M of NaCl.

In this step, about 90% of plasminogen-dependent fibrinolytic activity applied to the column was eluted. However, only less than 5% of radioactivity applied to the column was detected in this fraction. tPA having a molecular weight of 70,000 daltons was detected by zymography after SDS polyacryamide gel electrophoresis.

The remaining protein was attempted to desorb with a 0.M Tris-HC( buffer (pH 9.0) which contained 3 M of ammonium thiocyanate and 0.2% of "Tween 80".

About 5% of plasminogen-dependent fibrinolytic activity applied to the column was measured, however, almost 90% of radioactivity applied to the column was detected in this fraction.

A conclusion was thus derived from the above results that chinese hamster tPA and human tPA can be separated by using the affinity column of ETI.

EXAMPLE 4

Mouse fibroblasts (C127I, ATCC CRL 1616 cells) can be used as host cels upon production of tPA in accordance with the recombinant DNA technology. After stabilizing with 0.02% of "Tween 80" (trade name) 3 l of a cultured broth of the wild-type strain which contained 2% of thermoinactivated (56° C., 30 minutes) fetal calf serum, it was subjected to one of the above-prepared affinity columns.

The column effluent was collected and the measured. No tPA was detected.

After passing the whole cultured broth through the column, the column was washed with 20 volumes (relative to the column capacity) of a 0.1M $NH_4HCO_3$ buffer (pH 7.5) which contained 1.5M NaCl and 0.2% of "Tween 80". By this method, almost 100% of the activity applied to the column was detected. tPA having a molecular weight of 70,000 daltons was detected by zymography after SDS polyacrylamide gel electrophoresis.

The column was eluted under the same conditions as those used routinely for the elution of human-derived tPA but no tPA was detected. The column was then washed with 10 volumes (relative to the column capacity) of a 4M $NH_4SCN$ solution which contained 0.2% of "Tween 80" but no tPA was eluted by this method. From these facts, the binding strength of C127-derived tPA to the affinity reagent was confirmed to be different from that of human tPA.

Separately, a mouse tPA fraction obtained in the above-described manner was labeled with $I^{125}$, followed by its addition to 0.5 % of a cultured broth of C127I cells in which the human tPA gene had been integrated. The broth contained 2% of thermoinactivated (56° C., 30 minutes) fetal calf serum. After stabilizing the resultant mixture with 0.02 % of "Tween 80", it was passed through one of the above-prepared column The column effluent was collected and the plasminogen-dependent fibrinolytic activity and radioactivity were measured Although the fibrinolytic activity was not detected, about 10% of the radioactivity applied to the column was detected After passing the whole cultured broth through the column, the column was washed with a 0.1M $NH_4HCO_3$ buffer (pH 7.5) which contained 1.5M of NaCl and 0.2% of "Tween 80". Although fibrinolytic activity as low as about 10% of the fibrinolytic activity applied to the column was detected by the above method, radioactivity as much as about 90% of the radioactivity applied to the column was recovered.

The eluate was analyzed by zymography subsequent to its electrophoresis in SDS. Bands corresponding respectively to 110,000 ± 20,000 daltons and 70,000 daltons were observed. Radioactivity was detected only from the protein of 70,000 daltons. Thereafter, the protein was eluted with a 0.1M glycine hydrochloride buffer (pH 3.5) containing 0.1M of NaCl. In this manner, the remaining plasminogen-dependent fibrinolytic activator was eluted and about 90% of the fibrinolytic activity applied to the column was detected. However, substantially no radioactivity was detected.

A conclusion was thus derived from the above results that mouse tPA and human tPA can be separated by using the affinity column. This conclusion was consistent with the fact that the single fraction of 70,000 daltons was solely separated and obtained out of the tPA derived from normal human cells in the final step of Example 4.

What is claimed is:

1. A method of purifying crude human tissue plasminogen activator (tPA) containing, as an impurity, a protein which is reactive with an anti-human tPA antibody and has a molecular weight of 110,000 ± 20,000 daltons, existing in a culture medium containing serum, which method consists essentially of the steps of:
    (a) passing the crude tPA to be purified through a column of an affinity reagent containing an immobilized Kunitz inhibitor which is produced in seeds of *Erythrina latissima* and other *Erythrina* plants and acts as an inhibitor to trypsin, plasmin and tPA but not to urokinase, to thereby bind the tPA to the affinity reagent and separate unbound material
    (b) washing the column with a saline buffer solution containing salts at neutral or alkaline pH containing 0.5 to 3.0M NaCl; and thereafter
    (c) eluting the tPA-bound affinity reagent with a buffer of acidic pH.

2. The method as claimed in claim 1, wherein the crude tPA is produced by a transformant strain obtained by using non-human animal cells as host cells and integrating the human tPA gene therein, and the tPA-bound affinity reagent is eluted to produce tPA in a purified form free of protein having the molecular weight of 110,000 ± 20,000 daltons and tPA derived from the non-human cells.

3. The method as claimed in claim 1, wherein the tPA is secreted from culture cells derived form melanoma cells.

4. The method as claimed in claim 1, wherein said tPA is secreted from culture cells derived from normal human tissues.

5. The method as claimed in claim 1, wherein said tPA is secreted from culture cells obtained by integrating the human tPA gene using recombinant DNA technology.

6. The method as claimed in claim 5, wherein said human tPA gene is derived from melanoma cells.

7. The method as claimed in claim 5, wherein said human tPA gene is derived from normal human tissues.

8. The method as claimed in claim 5, wherein said tPA is produced by a transformant strain obtained using mammalian cells as host cells and integrating the human tPA gene therein.

9. The methods as claimed in claim 8, wherein said mammalian cells are mouse fibroblast (C127).

10. The method for preparing purified human tissue plasminogen activator (tPA) free of a protein which is reactive with an anti-human tPA antibody and has a molecular weight of 110,000 ± 20,000 daltons, said method consisting essentially of the steps of:
    (A) cultivating a tPA-yielding transformant strain non-human animal cell culture obtained by integrating the human tPA gene in the animal cells in a suitable culture medium containing fetal bovine serum;
    (B) allowing the tPA-yielding cells to secrete tPA in the presence of fetal bovine serum to produce tPA together with a protein which is reactive with an anti-human tPA antibody and has a molecular weight of 110,000 ± 20,000 daltons;

(C) passing the tPA-containing mixture of step (B) through a column of an affinity reagent containing an immobilized Kunitz inhibitor which is produced in seeds of *Erhthrina latissima* and other *Erythrina* plants and acts as an inhibitor to trypsin, plasmin and tPA but not to urokinase, to thereby bind the tPA to the affinity reagent and separate unbound material, (D) washing the column with saline buffer solution containing salts at neutral or alkaline pH containing 0.5 to 3.0M NaCl;

(E) eluting the tPA-bound affinity reagent with a buffer of acidic pH; and (F) collecting the tPA in substantially pure form essentially free from the 110,000 ± 20,000 daltons protein.

* * * * *